(12) United States Patent
Doron et al.

(10) Patent No.: US 7,522,962 B1
(45) Date of Patent: Apr. 21, 2009

(54) IMPLANTABLE MEDICAL DEVICE WITH INTEGRATED ACOUSTIC TRANSDUCER

(75) Inventors: Eyal Doron, Kiryat Yam (IL); Abraham Penner, Tel Aviv (IL)

(73) Assignee: Remon Medical Technologies, Ltd, Caesarea (IL)

( * ) Notice: Subject to any disclaimer, the term of this patent is extended or adjusted under 35 U.S.C. 154(b) by 710 days.

(21) Appl. No.: 11/293,414

(22) Filed: Dec. 2, 2005

Related U.S. Application Data (60) Provisional application No. 60/633,063, filed on Dec. 3, 2004.

(51) Int. Cl.
*A61N 1/00* (2006.01)
(52) U.S. Cl. .................................................. 607/60
(58) Field of Classification Search .............. 607/32, 607/60; 600/486
See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Massa |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |
| 4,227,407 A | 10/1980 | Drost |
| 4,281,484 A | 8/1981 | Massa |
| 4,431,873 A | 2/1984 | Dunn et al. |
| 4,433,400 A | 2/1984 | De Reggi et al. |
| 4,456,850 A | 6/1984 | Inoue et al. |

(Continued)

FOREIGN PATENT DOCUMENTS

DE 3222349 1/1984

(Continued)

OTHER PUBLICATIONS

Blevins Ph.D., "Formulas for Natural Frequency and Mode Shape", ISBN: 1-57524-184-6. (1979).

(Continued)

*Primary Examiner*—Carl H Layno
*Assistant Examiner*—Yun Haeng Lee
(74) *Attorney, Agent, or Firm*—Faegre & Benson LLP (57) ABSTRACT

An implantable medical device comprises a hermetically sealed housing having at least one hermetic electrical feed through and an acoustic lead having a proximal end connected to the electrical feed through. One or more acoustic transducers are carried in a distal portion of the acoustic lead and configured for converting energy between electrical energy and acoustic energy, wherein electronics for driving the one or more transducers are carried in the housing.

20 Claims, 6 Drawing Sheets

U.S. PATENT DOCUMENTS

| | | | |
|---|---|---|---|
| 4,481,950 A | 11/1984 | Duggan | |
| 4,517,665 A | 5/1985 | De Reggi et al. | |
| 4,519,401 A | 5/1985 | Ko et al. | |
| 4,541,431 A | 9/1985 | Ibrahim et al. | |
| 4,558,249 A | 12/1985 | Lerch et al. | |
| 4,580,074 A | 4/1986 | Gilman | |
| 4,593,703 A | 6/1986 | Cosman | |
| 4,600,855 A | 7/1986 | Strachan | |
| 4,642,508 A | 2/1987 | Suzuki et al. | |
| 4,653,036 A | 3/1987 | Harris et al. | |
| 4,653,508 A | 3/1987 | Cosman | |
| 4,660,568 A | 4/1987 | Cosman | |
| 4,672,976 A | 6/1987 | Kroll | |
| 4,676,255 A | 6/1987 | Cosman | |
| 4,677,337 A | 6/1987 | Kleinschmidt et al. | |
| 4,781,715 A | 11/1988 | Wurzel | |
| 4,793,825 A | 12/1988 | Benjamin et al. | |
| 4,835,435 A | 5/1989 | Yeung et al. | |
| 4,846,191 A | 7/1989 | Brockway et al. | |
| 4,911,172 A | 3/1990 | Bui et al. | |
| 4,958,100 A | 9/1990 | Crawley et al. | |
| 5,012,815 A | 5/1991 | Bennett, Jr. et al. | |
| 5,024,224 A | 6/1991 | Engebretson | |
| 5,088,576 A | 2/1992 | Potthoff et al. | |
| 5,113,859 A | 5/1992 | Funke | |
| 5,160,870 A | 11/1992 | Carson et al. | |
| 5,178,153 A | 1/1993 | Einzig | |
| 5,283,397 A | 2/1994 | Pavlovic | |
| 5,289,821 A | 3/1994 | Swartz | |
| 5,300,875 A | 4/1994 | Tuttle | |
| 5,314,457 A | 5/1994 | Jeutter et al. | |
| 5,339,290 A | 8/1994 | Greenstein | |
| 5,367,500 A | 11/1994 | Ng | |
| 5,381,067 A | 1/1995 | Greenstein et al. | |
| 5,381,386 A | 1/1995 | Lum et al. | |
| 5,410,587 A | 4/1995 | Grunwell | |
| 5,411,551 A | 5/1995 | Winston et al. | |
| 5,423,334 A | 6/1995 | Jordan | |
| 5,438,553 A | 8/1995 | Wilson et al. | |
| 5,476,488 A | 12/1995 | Morgan et al. | |
| 5,483,501 A | 1/1996 | Park et al. | |
| 5,488,954 A | 2/1996 | Sleva et al. | |
| 5,495,137 A | 2/1996 | Park et al. | |
| 5,554,177 A | 9/1996 | Kieval et al. | |
| 5,562,714 A | 10/1996 | Grevious | |
| 5,571,152 A | 11/1996 | Chen et al. | |
| 5,628,782 A | 5/1997 | Myers | |
| 5,679,026 A | 10/1997 | Fain et al. | |
| 5,704,352 A | 1/1998 | Tremblay et al. | |
| 5,733,313 A | 3/1998 | Barreras, Sr. et al. | |
| 5,735,887 A | 4/1998 | Barreras, Sr. et al. | |
| 5,741,316 A | 4/1998 | Chen et al. | |
| 5,749,909 A | 5/1998 | Schroeppel et al. | |
| 5,757,104 A | 5/1998 | Getman et al. | |
| 5,792,195 A | 8/1998 | Carlson et al. | |
| 5,807,258 A | 9/1998 | Cimochowski et al. | |
| 5,825,117 A | 10/1998 | Ossmann et al. | |
| 5,832,924 A | 11/1998 | Archibald et al. | |
| 5,833,603 A | 11/1998 | Kovacs et al. | |
| 5,843,135 A | 12/1998 | Weijand et al. | |
| 5,873,835 A | 2/1999 | Hastings et al. | |
| 5,879,283 A | 3/1999 | Adams et al. | |
| 5,935,081 A | 8/1999 | Kadhiresan | |
| 5,956,292 A | 9/1999 | Bernstein | |
| 5,957,950 A | 9/1999 | Mockros et al. | |
| 5,967,986 A | 10/1999 | Cimochowski et al. | |
| 6,044,298 A | 3/2000 | Salo et al. | |
| 6,053,873 A | 4/2000 | Govari et al. | |
| 6,058,329 A | 5/2000 | Salo et al. | |
| 6,068,589 A | 5/2000 | Neukermans | |
| 6,082,367 A | 7/2000 | Greeninger et al. | |
| 6,140,740 A | 10/2000 | Porat et al. | |
| 6,141,588 A * | 10/2000 | Cox et al. | 607/9 |
| 6,185,452 B1 | 2/2001 | Schulman et al. | |
| 6,223,081 B1 | 4/2001 | Kerver | |
| 6,409,675 B1 | 6/2002 | Turcott | |
| 6,475,170 B1 | 11/2002 | Doron et al. | |
| 6,477,406 B1 | 11/2002 | Turcott | |
| 6,480,733 B1 | 11/2002 | Turcott | |
| 6,486,588 B2 | 11/2002 | Doron et al. | |
| 6,504,289 B2 | 1/2003 | Toda et al. | |
| 6,527,729 B1 | 3/2003 | Turcott | |
| 6,537,200 B2 | 3/2003 | Leysieffer et al. | |
| 6,554,761 B1 | 4/2003 | Puria et al. | |
| 6,575,894 B2 | 6/2003 | Leysieffer et al. | |
| 6,600,949 B1 | 7/2003 | Turcott | |
| 6,628,989 B1 | 9/2003 | Penner et al. | |
| 6,629,922 B1 | 10/2003 | Puria et al. | |
| 6,643,548 B1 | 11/2003 | Mai et al. | |
| 6,645,145 B1 | 11/2003 | Dreschel et al. | |
| 6,654,638 B1 | 11/2003 | Sweeney | |
| 6,671,550 B2 | 12/2003 | Iaizzo et al. | |
| 6,697,674 B2 | 2/2004 | Leysieffer | |
| 6,740,076 B2 | 5/2004 | Hoben et al. | |
| 6,741,714 B2 | 5/2004 | Jensen | |
| 6,763,722 B2 | 7/2004 | Fjield et al. | |
| 6,764,446 B2 | 7/2004 | Wolinsky et al. | |
| 6,772,490 B2 | 8/2004 | Toda | |
| 6,792,308 B2 | 9/2004 | Corbucci | |
| 7,016,739 B2 | 3/2006 | Bange et al. | |
| 7,024,248 B2 | 4/2006 | Penner et al. | |
| 7,035,684 B2 | 4/2006 | Lee | |
| 7,107,103 B2 | 9/2006 | Schulman et al. | |
| 7,114,502 B2 | 10/2006 | Schulman et al. | |
| 7,115,096 B2 | 10/2006 | Siejko et al. | |
| 7,118,531 B2 | 10/2006 | Krill | |
| 7,123,962 B2 | 10/2006 | Siejko et al. | |
| 7,127,290 B2 | 10/2006 | Girouard et al. | |
| 7,176,602 B2 | 2/2007 | Schlenke | |
| 7,198,603 B2 * | 4/2007 | Penner et al. | 600/486 |
| 7,220,232 B2 | 5/2007 | Suorsa et al. | |
| 7,228,175 B2 | 6/2007 | Jain et al. | |
| 7,236,821 B2 | 6/2007 | Cates | |
| 7,248,923 B2 | 7/2007 | Maile et al. | |
| 7,260,429 B2 | 8/2007 | Siejko et al. | |
| 7,273,457 B2 | 9/2007 | Penner | |
| 7,283,874 B2 | 10/2007 | Penner | |
| 7,335,169 B2 | 2/2008 | Thompson et al. | |
| 7,431,699 B2 | 10/2008 | Siejko et al. | |
| 2004/0106954 A1 | 6/2004 | Whitehurst et al. | |
| 2004/0122484 A1 | 6/2004 | Hatlestad et al. | |
| 2004/0127792 A1 | 7/2004 | Siejko et al. | |
| 2004/0138572 A1 | 7/2004 | Thiagarajan | |
| 2004/0204744 A1 * | 10/2004 | Penner et al. | 607/23 |
| 2004/0230249 A1 | 11/2004 | Haefner | |
| 2005/0131472 A1 | 6/2005 | Ding et al. | |
| 2005/0137490 A1 | 6/2005 | Scheiner et al. | |
| 2005/0149138 A1 | 7/2005 | Min et al. | |
| 2006/0009818 A1 | 1/2006 | Von Arx et al. | |
| 2006/0142819 A1 | 6/2006 | Penner et al. | |
| 2006/0149329 A1 * | 7/2006 | Penner | 607/32 |
| 2007/0049977 A1 | 3/2007 | Von Arx et al. | |
| 2007/0142728 A1 * | 6/2007 | Penner et al. | 600/486 |
| 2008/0021289 A1 | 1/2008 | Zhang et al. | |
| 2008/0021509 A1 | 1/2008 | Mi et al. | |
| 2008/0021510 A1 | 1/2008 | Mi et al. | |

FOREIGN PATENT DOCUMENTS

| | | |
|---|---|---|
| EP | 0798016 | 10/1997 |
| EP | 0897690 | 2/1999 |
| EP | 1151719 | 11/2001 |
| WO | WO 83/03345 | 10/1983 |
| WO | WO 97/01986 | 1/1997 |

| WO | WO 97/33513 | 9/1997 |
| WO | WO 97/35636 | 10/1997 |
| WO | WO 97/47236 | 12/1997 |
| WO | WO 98/26716 | 6/1998 |
| WO | WO 98/29030 | 7/1998 |
| WO | WO 99/26530 | 6/1999 |
| WO | WO 99/59460 | 11/1999 |
| WO | WO 00/16686 | 3/2000 |
| WO | WO 03/068047 | 8/2003 |
| WO | WO 2004/091719 | 10/2004 |
| WO | WO 2006/069215 | 6/2006 |

OTHER PUBLICATIONS

C. Hierold et al (Germany, 1998) "Implantable Low Power Integrated Pressure Sensor System for Minimal Invasive Telemetric Patient Monitoring" IEEE, pp. 568-573.

Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.

ER. Cosman et al (Massachussetts, Apr. 1979) "A Telemetric Pressure Sensor for Ventricular Shunt Systems" Surgical Neurology, vol. 11, No. 4, pp. 287-294.

Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.

Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.

G. W. H. Schurink et al (1998) "Late Endoleak after Endovascular Therapy for Abdominal Aortic Aneurysm" Eur. J. Vasc. Endovasc. Surg. vol. 17, pp. 448-450.

GH White et al (1997) "Endoleak Following Endoluminal Repair of AAA: Management Options and Patient Outcomes", J. Endovasc Surg. p. I-45.

Karl E. Richard et al (Germany, Jan. 1999) "First clinical results with a telemetric shunt-integrated ICP-sensor" Neurological Research vol. 21, pp. 117-120.

Prof. Dr. Johannes Zacheja et al (Germany, Sep. 1996) "An Implantable Microsystem for Biomedical Applications" Micro System Technologies 96, pp. 717-722.

S. K. Gupta et al (1999) "Use of a Piezoelectric Film Sensor for Monitoring Vascular Grafts" The American Journal of Surgery vol. 160, pp. 182-186.

T. Chuter et al (Sweden, Jan. 1997) "Aneurysm Pressure following Endovascular Exclusion" Eur. J. Vasc. Endovasc. Surg. vol. 13, pp. 85-87.

T.A. Cochran et al (1990) "Aortic Aneurysm Abdominal", Current Therapy in Adult Medicine, Fourth Edition.

Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.

Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

* cited by examiner

IMPLANTABLE MEDICAL DEVICE WITH INTEGRATED ACOUSTIC TRANSDUCER

RELATED APPLICATION DATA

The present application claims the benefit of priority under 35 U.S.C § 119 to U.S. Provisional Application 60/633,063, filed Dec. 3, 2004, the contents of which are hereby incorporated by reference.

FIELD OF INVENTION

The present invention relates to the field of diagnostic and therapeutic medical implants and data communication between them.

BACKGROUND

Communication between diagnostic and/or therapeutic medical device implants within the body can be highly beneficial. One example is the information exchange between an implantable sensor and an implantable pulse generator (IPG), that uses the sensed information for optimizing its operation. Published U.S. Patent Application US 2004-0204744A1, which is incorporated by reference herein, discloses using an intra-body acoustic communication link for this purpose. As taught in that publication, in order to minimize energy consumption, the sensor implant is left deactivated (i.e., not powered on) until an acoustic wave pulse received from another implanted device activates the sensor implant using acoustic switch technology. Two possible transducer configurations applicable for this concept are disclosed in this published application.

Acoustic transducers integrated in implantable medical device are known. For example, U.S. Pat. No. 6,477,406, discloses several acoustic transducer configurations used for listening to sounds produced by the heart. However, these transducers were designed only for receiving acoustic signals, and not for transmitting acoustic signals. Moreover, the transducer configurations of this patent are optimized to low sound frequencies in a range of 5-300 Hz, while for acoustic communication much higher frequencies are used, e.g., in an ultrasonic range of 20 kHz-10 MHz. In particular, U.S. Pat. No. 6,477,406 does not teach an acoustic transducer that can effectively produce ultrasonic transmission or to serve as an effective receiver at high acoustic frequencies.

Acoustic communication was also suggested for data exchange between an implantable device and external unit, such as disclosed in U.S. Pat. No. 5,113,859. However, this patent also does not teach or describe an acoustic transducer capable of performing the communication, nor is there any transducer disclosed or described that is capable of transmitting ultrasonic signals at a level sufficient for activating an acoustic switch and or communicating with a second implant.

BRIEF DESCRIPTION OF THE DRAWINGS

The drawings illustrate the design and utility of embodiments of the invention, in which similar elements are referred to by common reference numerals. With the understanding that these drawings depict only exemplary embodiments of the invention, and are not therefore to be considered limiting its scope, the embodiments will be described and explained with additional specificity and detail through the use of the accompanying drawings, in which.

DETAILED DESCRIPTION OF THE ILLUSTRATED EMBODIMENTS

The present invention is directed to an (active) implantable medical device such as a pacemaker, implantable cardioverter defibrillator (ICD), Cardiac Rhythm Therapy (CRT), a standalone hemodynamic monitor, or implantable drug pump, which communicates with another implanted device (not shown), or an extracorporeal device (not shown), using an acoustic communication link. Towards this end, the active implantable device is provided with an acoustic transducer capable of transmitting an acoustic pulse sufficient for activating an acoustic switch in the receiving device, such as described in U.S. Pat. No. 6,628,989. For this purpose, an acoustic pulse that is at least 0.1 msec wide, and at least a 50 Pa peak pressure is preferred. For example, a pulse of 0.5 msec and 500 Pa may be used in one embodiment. The acoustic transducer is preferably capable of transmitting acoustic pulses at a pressure of at least 0.05 Pa (measured at 20 cm in vitro) and receiving signals of 0.05 Pa. The frequency range at which the system can operate is preferably within a range of 20 KHz-3 MHz. In order to maximize the efficiency of the transducer, it is preferably designed to operate at its resonance frequency.

The acoustic transducer may be constructed on an internal surface of the implantable device housing, typically a hermetically sealed enclosure, with a portion of the enclosure housing wall coupled to the transducer and acting as a vibrating diaphragm. Several examples of such embodiments are disclosed and described in co-pending U.S. patent application Ser. No. 11/287,557, filed Nov. 23, 2005, entitled "Implantable Medical Device With Integrated Acoustic Transducer," the disclosure of which is hereby incorporated by reference in its entirety.

Integrating the acoustic transducer within the medical device enclosure is practically transparent to the implanting physician. Also in this configuration the hermetic enclosure protects the transducer and its electronics from the environment. However, usually the implantation location of the active medical device is limited due to its size and the wish to minimize the implantation procedure invasiveness. As a result the implantation site can be sub-optimal for acoustic communication. For example, an IPG is most often implanted under the skin beneath the collar bone. Due to anatomy and the physical fact that acoustic waves can not cross the lungs any communication between the IPG and a second implant located within the heart may be sub-optimal.

Figure 1:
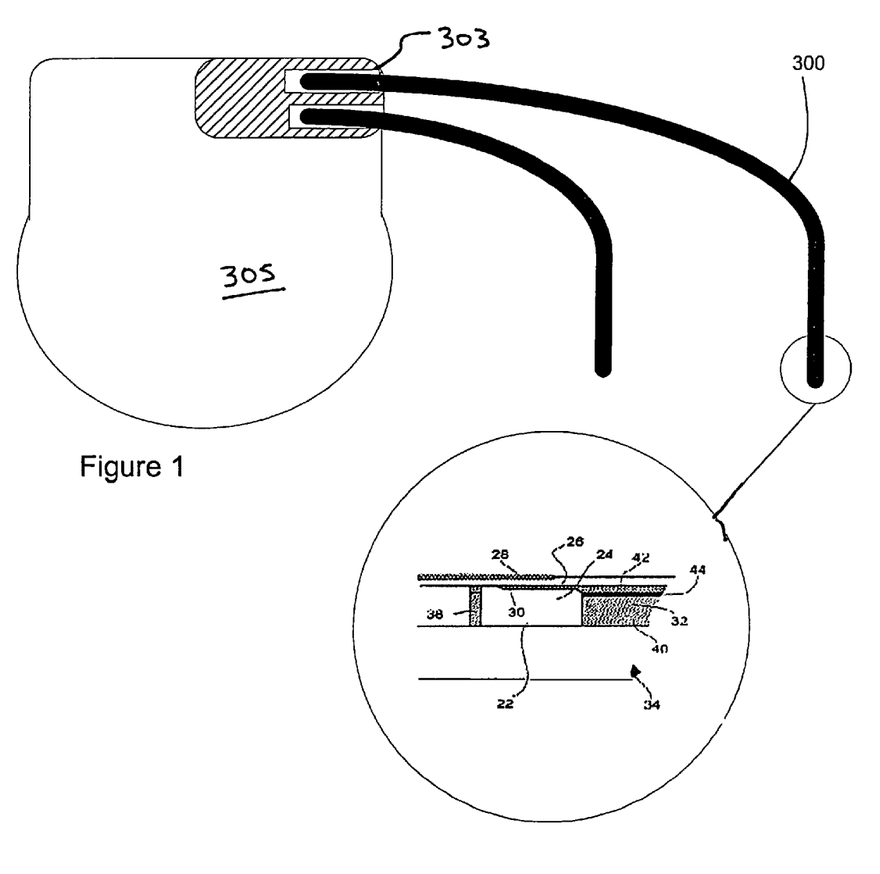
FIG. 1 depicts an exemplary embodiment of an acoustic transducer integrated on an end of an implantable acoustic lead.

FIG. 1 illustrates one embodiment of the invention, in which the linkage between the location of an IPG and that of the transducer is disconnected. In particular, an acoustic transducer is located at the tip of a lead 300, referred to herein as an "acoustic lead." The acoustic lead 300 can be similar to an electrical lead commonly used in IPGs (e.g., for pacing). In a preferred embodiment, the acoustic lead 300 is not positioned within the heart, but rather in a vein leading to the right atrium, e.g. the subclavian vein, the cephalic vein, the right or left brachiocephalic vein, the superior or inferior vena cava or the internal jugular vein. The connection of the said acoustic lead 300 to an IPG 305 can be via a standard electrical hermetic feed through 303 of the IPG 305.

Implantation of the acoustic lead 300 can be performed using the same catheterization techniques used for implanting IPG electrical leads. However, instead of entering the right atrium (and in some cases the heart right ventricle), the acoustic lead can preferably be located external to the heart, and preferably in a location with a direct "line of sight" between the lead acoustic source and a second implant to be in communication with the transducer. Many of the risks involved in implanting an IPG electrical lead, such as thrombus formation or damage to the heat valve, may be avoided by not entering the heart or passing through the heart valve. The fixation of the acoustic lead 300 may be accomplished, for example, by a radial anchoring of the device to a wall of the vessel using a stent-like device, or with a screw or hook-type fixation to the vessel wall.

Alternatively the lead can be implanted at other positions not via catheterization, for example under the skin, or taking advantage of the cut required for implanting the IPG, the lead can be positioned in the cut and aligned optimally to the implant in order to optimize the acoustic channel. The connection of the said acoustic lead to the IPG can be via a standard electrical feed through of the IPG. The implantation of the acoustic lead can be using the same technique of catheterization used for implanting IPG electrical leads. However, preferably instead of entering the right atrium and in some cases the heart right ventricle, the acoustic lead can be located external to the heart, preferably in a location with a direct line of sight between the lead acoustic source and the second implant. Many of the risks involved in implanting an IPG electrical lead, such as thrombus formation or damage to the heat valve, may be avoided by not entering the heart or passing through the heart valve.

The transducer in FIG. 1 is based on the design disclosed in U.S. Pat. No. 6,140,740, the contents of which are fully incorporated herein by reference. The transducer may be manifested as a single transducer or as an array of such transducers, used mainly for transforming acoustic energy into electrical energy. The transducer(s) generally include (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of the acoustic interrogation signal; and (iii) a first electrode attached to the external surface and a second electrode attached to the internal surface.

The piezoelectric layer is preferably of a material selected from the group consisting of PVDF and piezoceramic. A transducer based on this design can produce approximately 100 Pa for 100 volts of excitation voltage. Since the transducer is made of a PVDF or a similar material, it can withstand much higher voltages. As a result, the transmission acoustic requirements for activating an acoustic pulse can be easily met with such a transducer at a voltage of several hundreds of volts. The high voltage required can be produced in the IPG or more preferably close to the transducer using a transformer of similar step up voltage device known in the art.

Figure 2:
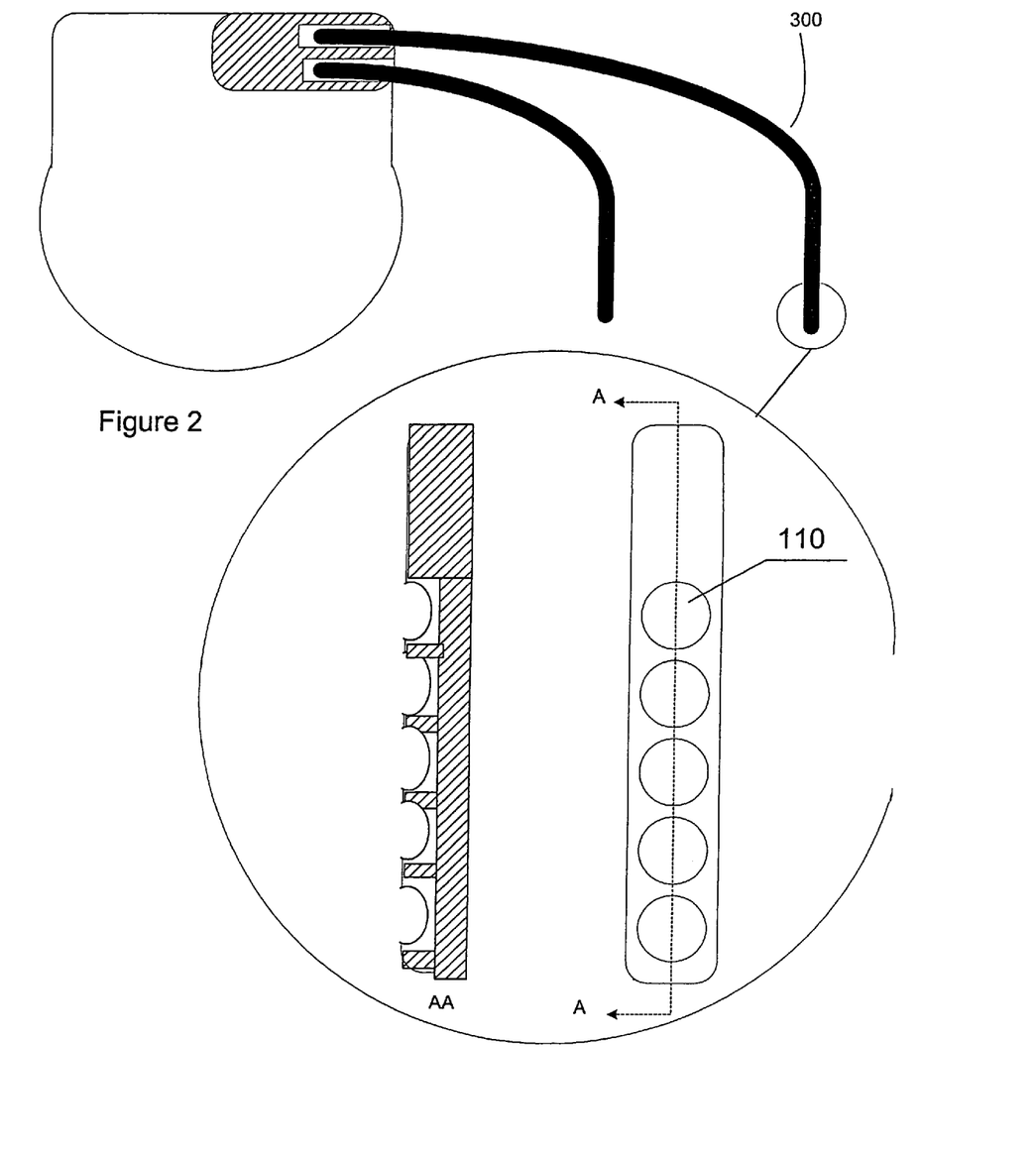
FIGS. 2, 2a, 2b and 2c depict alternate embodiments of an acoustic transducer integrated on an end of an implantable acoustic lead.
Figure 2A:
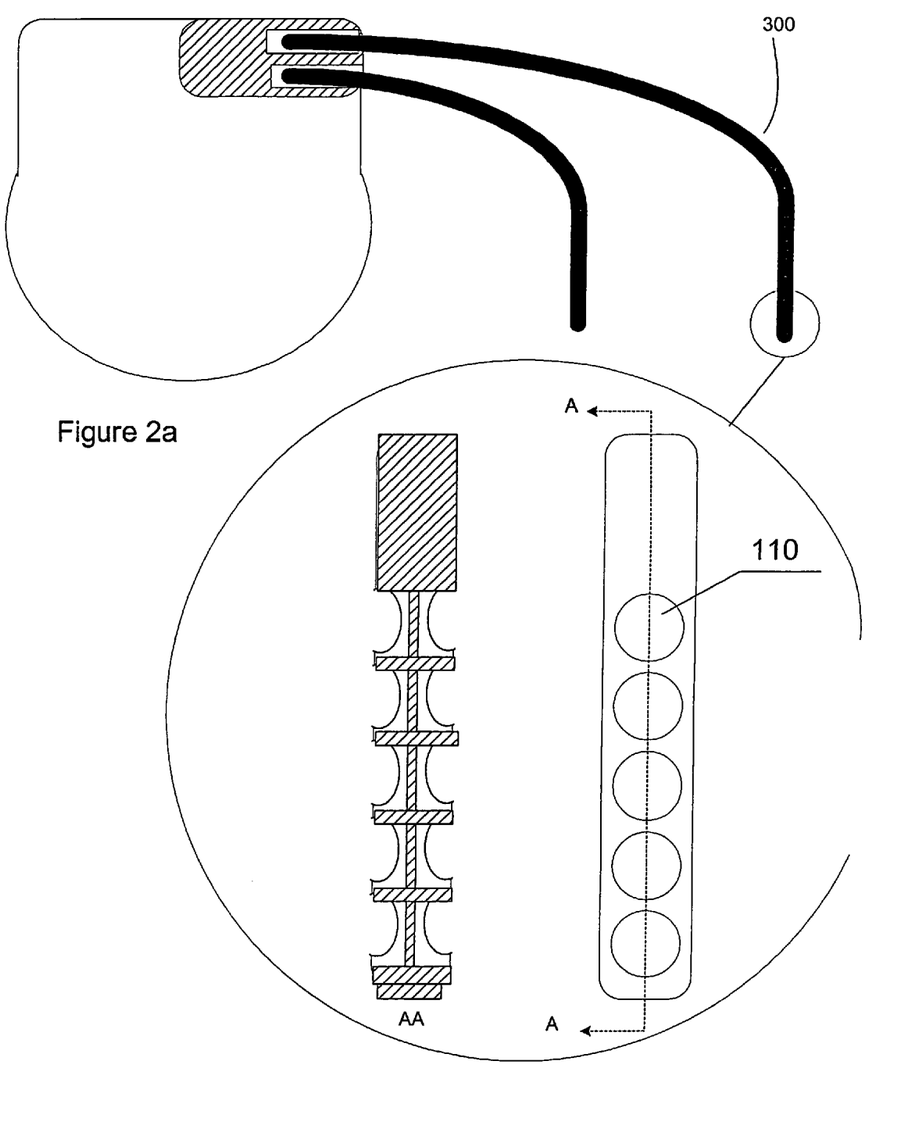

FIGS. 2 & 2a disclose alternative transducer designs that can substantially reduce the high voltage requirement of the transducer design proposed in FIG. 1. The design is based on providing an array of transducers, such as the transducer of FIG. 1. Several such transducers may be connected in parallel in order to increase the transmitted pressure. Since each of the proposed transducer is relatively small (about 2 mm in diameter), several such transducers can be integrated into a lead of less than 12 Fr, or even less than 8 Fr. with minimal compromising on the lead flexibility.

Figure 2B:
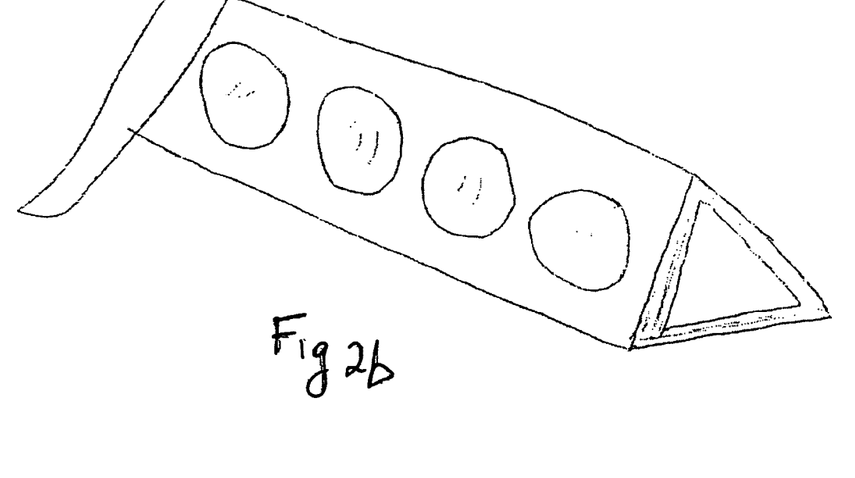
Figure 2C:
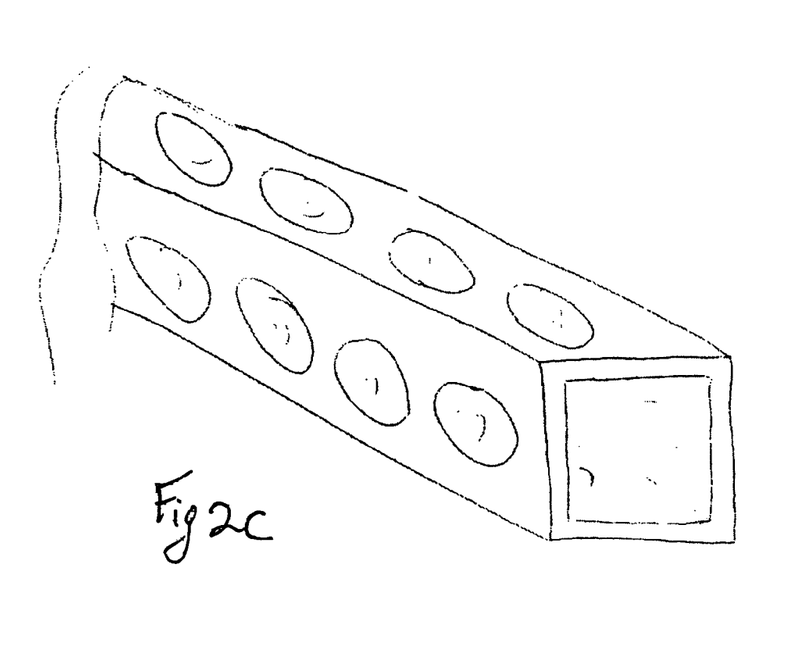

The array can be single sided, as shown in FIG. 2, or double sided as shown in FIG. 2a. Since the proposed transducer thickness is about 1 mm or less, other configurations are possible in which bars of transducer array are assembled together forming geometric form of a triangle (FIG. 2b), or a square (FIG. 2c), or other forms such as a pentagon, hexagon or even more complex configurations. The specific number of acoustic cell members on each face (4 are shown) may vary in a range between 1-20 cells per face. These proposed array assemblies have the advantage of increasing the number of acoustic cells while retaining a low lead diameter. Since the connection between the acoustic cell members can be flexible the resulted lead can also be highly flexible.

Since the physical behavior of an array of transducers may vary from that of the single transducer due to the mutual effect imposed by the neighboring cells, the cell members in the array may be connected in parallel to the same driver or may have separate power sources which have different phases and/or voltage amplitude for optimizing the transmitted acoustic pulse. Also, each of the acoustic cell members can have different acoustic response characteristics, e.g. resonance frequency and resonance width, so as to optimize the acoustic response for the specific application.

Figure 3A:
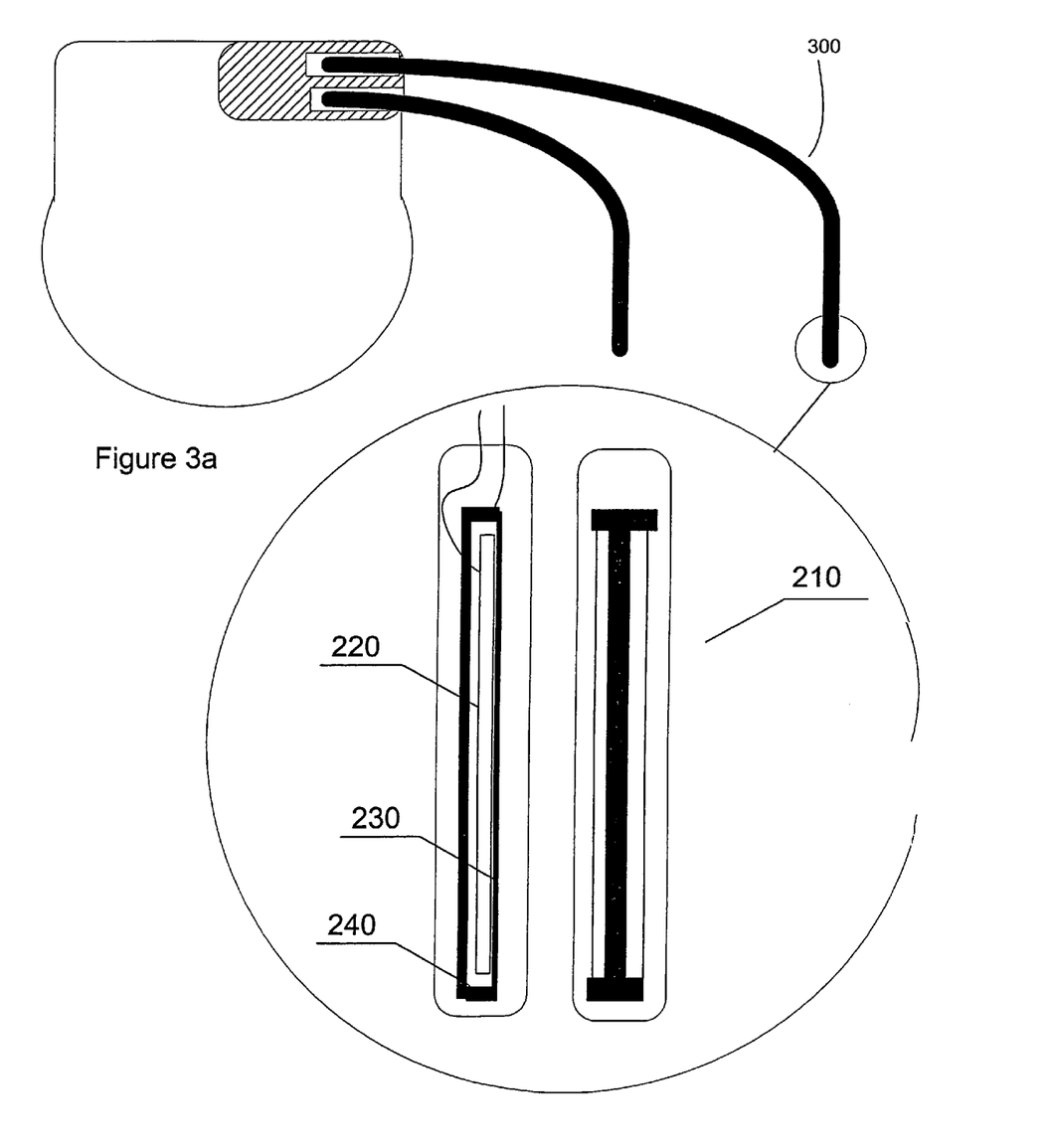
FIGS. 3a and 3b illustrate still further alternate embodiments of an acoustic transducer integrated on an end of an implantable acoustic lead, in which the transducer is based on a piezoelectric ceramic bar coupled to a flat surface acting as a membrane.
Figure 3B:
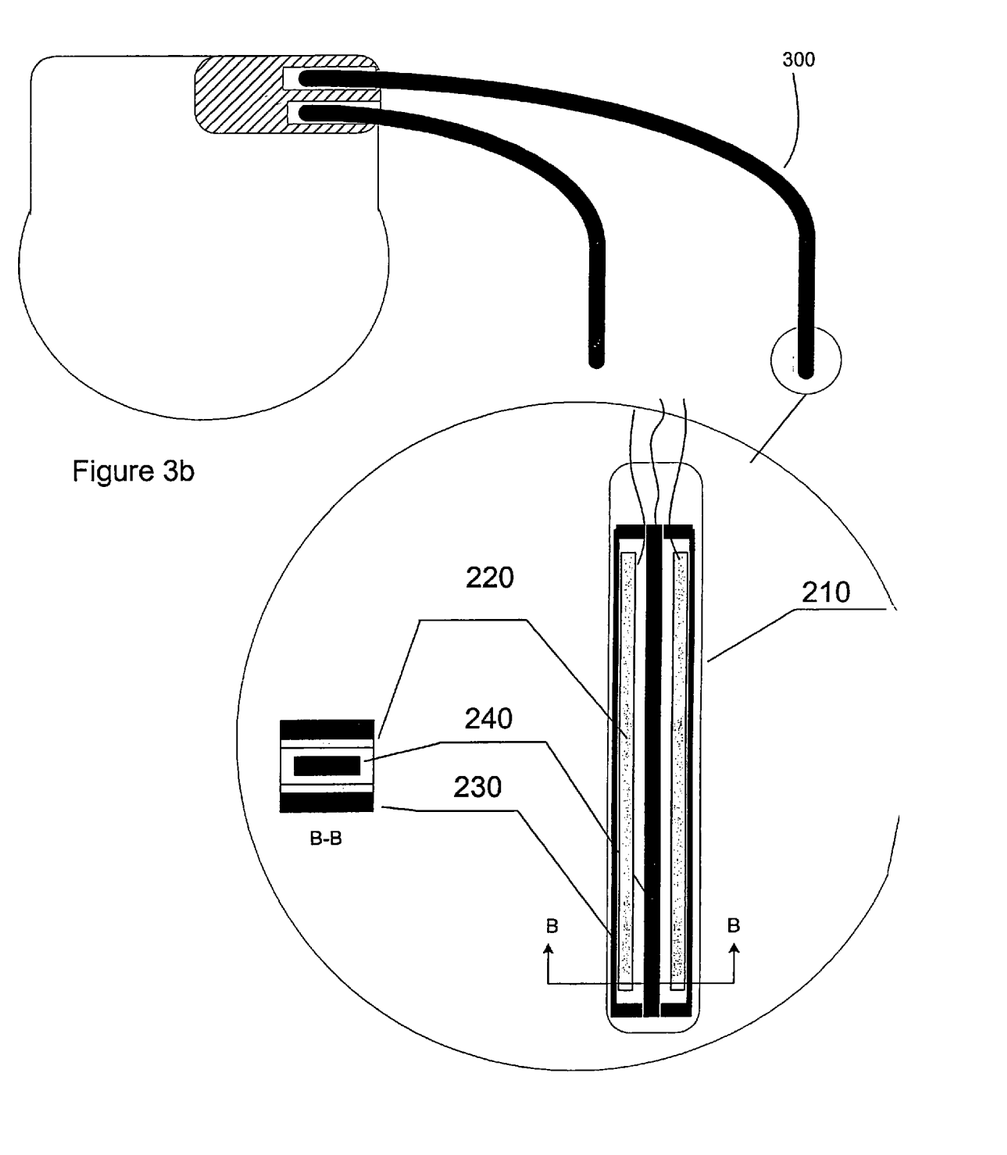

FIGS. 3a and 3b illustrate a transducer that is based on a piezoelectric ceramic bar coupled to a flat surface acting as a membrane. The length of the structure is fixed by a rigid backbone, whereas preferably the entire structure is vibrating at its resonance frequency. FIG. 3a discloses such an acoustic transducer structure in which a piezoelectric bar (220) (alternatively built from pieces of ceramic) is coupled to the internal diaphragm (230), preferably a metallic one. A means for fixing the length of the structure should be implanted such as the proposed bar (240) in FIG. 3a. An additional configuration of such a transducer is disclosed in FIG. 3b. This design has two transducers, which are based on the design suggested in FIG. 3a. In this design the fixation bar (240) is in the center of the structure.

It will be appreciated that the illustrated embodiments are by way of example, and not limitation, and other and further transducer embodiments may be employed within the scope of the inventions disclosed herein.

Piezoelectric materials are well known and the proposed design of the transducer can use any material from the group including: electrostrictive ceramic, piezoelectric ceramic, piezoelectric ceramic-polymer composite and piezoelectric polymers. The proposed transducer design can employ one or more piezoelectric discs with an electrode there between discs, e.g., two discs surrounding an electrode. This configuration allows for electrical connection of the piezoelectric discs in series, in parallel, or in a combination of the two, using electrical contacts to the disc electrodes. This configuration allows optimization of the transducer for specific tasks. For example, the voltage available in an IPG is usually relatively low, produced from its internal 2-3 volts battery. For transmitting an acoustic signal required for activating an acoustic switch, a relatively high voltage may be required (for example, several hundred volts).

Using multiple, thin discs of piezoelectric material connected in parallel will produce the equivalent acoustic power of a single, thicker disc, but at a substantially lower voltage. For example, two piezoelectric discs that are each 0.5 mm thick, connected in parallel, will produce a similar acoustic power as a 1 mm thick piezoelectric disc at half the voltage. However, if one wishes to optimize the receiving sensitivity of the transducer, serial connection of the thin piezoelectric discs will result in a higher voltage signal per a given acoustic signal, than a single thick disk. The ceramics may also be connected anti-parallel, to produce a bending moment as a piezoelectric bimorph.

For producing the transmitted acoustic signal, the proposed acoustic transducer should be efficient and durable. Preferably, the transducers should work at their resonance frequency in order to optimize the efficiency and sensitivity of the transducer. The resonance frequency of the transducer depends on several parameters, including the type, thickness and diameter of the piezoelectric material, the material and thickness of the diaphragm (230), and the material, thickness, and height of the rigid wall 240, as is known by those skilled in the art of acoustic transducer design.

For optimizing the receiving sensitivity of the transducer, a separate piece of piezoelectric material with relatively high acoustic sensitivity can be used, such as a layer of PVDF (not shown), attached to the piezoelectric ceramic disc/s used for transmission. Another way to improve the receiving signal to noise is by integrating an amplifier close to the structure or within the lead in order to minimize any parasitic effects and noises.

All the above-disclosed, implantable transducers can, in addition to activation and communication with a second implant, also be used for acoustically energizing and charging the second implant. Preferably, the acoustic lead design of FIG. 1 should be used for this purpose, taking advantage of the optimized location of the transducer in these configurations relative to the second implant. The possible line of sight between the lead transducer and the second implant, combined with the possible small distance between them, which can be between a few millimeters to several centimeters, can significantly reduce the required energy for charging the second implant battery or capacitor. The charging can be done using energy from the IPG battery, or from an extracorporal power source (either telemetrically, or by making a small incision at the IPG implantation site), disengaging the acoustic lead from the IPG controller, connecting the acoustic lead to an external power source, and using the acoustic energy produced by the acoustic lead to charge the battery within the second implant.

Preferably, the battery capacity of the second implant is such that charging will not be required for a duration longer than that of the IPG battery. Upon the replacement of the IPG controller, the acoustic lead can be connected to an external power source for charging the second implant battery. Alternatively, an acoustic catheter can be used for acoustically charging the second implant. This catheter can be built similar to the acoustic lead, with an acoustic transducer at its tip or by serving as an acoustic wave-guide. The acoustic catheter can be introduced to the body in a similar technique used for right heart catheterization. This procedure is usually carried out via the femoral vein and internal jugular subclavian vein, using a standard guide wire based catheterization or by a floating balloon (e.g., a Swan-Ganz catheter). The procedure can be guided using fluoroscopy or pressure pattern measurements. Since the acoustic source on the catheter can be located very close to the second implant, the charging process is preferably very efficient and local.

The transducer designs disclosed herein are preferably encapsulated as required for an implantable active medical device. Methods of manufacturing electrical leads for IPG are well known in the art, and one may use such known methods, and materials such as polyurethane or silicone extrusion, for encapsulating the transducer and its supporting electronics. Alternatively, the transducer may be encapsulated in a metallic sealed case filled with inert liquid (e.g. silicone oil) and having at least one flexible face. Such a metallic box can be made from any biocompatible metal such as titanium, tantalum, stainless steel, gold or platinum with a flexible membrane preferably less the 0.5 mm thick and more preferably less than 0.05 mm thick.

What is claimed:

1. An implantable medical device, comprising:
   a hermetically sealed housing having at least one hermetic electrical feed through;
   an acoustic lead having a proximal end connected to the electrical feed through;
   one or more acoustic transducers carried in a distal portion of the acoustic lead and configured for converting energy between electrical energy and acoustic energy; and
   electronics carried in the housing for driving the one or more transducers.

2. The device of claim 1, wherein the one or more transducers are further configured for acoustic communication with another implantable medical device.

3. The device claim 1, the one or more transducers comprising:
   a diaphragm having a width, thickness and length, a piezoelectric material having a rectangular shape coupled to said diaphragm,
   means for keeping the length of the diaphragm substantially unchanged, and
   means for electrically activating the piezoelectric material in order to induce movement of the diaphragm.

4. The device of claim 3, wherein the diaphragm comprises a metal having a thickness of approximately 0.1 mm to 5 mm.

5. The device of claim 3, wherein the diaphragm comprises a metal having a width of approximately 0.4 mm to 8 mm.

6. The device of claim 3, wherein the diaphragm comprises a metal having a length of 0.5 mm to 25 mm.

7. The device of claim 3, wherein the piezoelectric material has a thickness of between 0.05 mm to 5 mm.

8. The device of claim 3, wherein the piezoelectric material has a width of between 0.3 mm to 8 mm.

9. The device of claim 3, wherein the piezoelectric material has a length of between 0.05 mm to 25 mm.

10. The device of claim 1, wherein the one or more transducers comprises an array of transducers.

11. The device of claim 1, wherein the distal portion of the acoustic lead comprises a bar, and wherein the one or more acoustic transducers comprises a single acoustic transducer.

12. The device of claim 1, wherein the distal portion of the acoustic lead comprises a bar, and wherein the one or more acoustic transducers comprises an array of transducers.

13. The device of claim 12, wherein the array of transducers is a single-side array of transducers.

14. The device of claim 12, wherein the array of transducers is a double-sided array of transducers.

15. The device of claim 1, wherein the distal portion of the acoustic lead comprises a plurality of bars each including one or more acoustic transducers.

16. The device of claim 15, wherein the plurality of bars form a triangular-shaped structure.

17. The device of claim 15, wherein the plurality of bars form a square-shaped structure.

18. The device of claim 1, wherein the one or more acoustic transducers includes at least one piezoelectric bar coupled to a membrane.

19. An implantable medical device, comprising:
   a hermetically sealed housing having at least one hermetic electrical feedthrough;

an acoustic lead having a proximal portion coupled to the electrical feedthrough;
a plurality of acoustic transducers each carried in a distal portion of the acoustic lead and configured for converting energy between electrical energy and acoustic energy; and
electronics carried in the housing for driving the one or more transducers.

20. An implantable medical device, comprising:
a hermetically sealed housing having at least one hermetic electrical feedthrough;
an acoustic lead having a proximal portion connected to the electrical feedthrough;
one or more acoustic transducers carried in a distal portion of the acoustic lead and configured for converting energy between electrical energy and acoustic energy, the one or more transducers including a piezoelectric material coupled to a diaphragm, a means for keeping the length of the diaphragm substantially unchanged, and a means for electrically activating the piezoelectric material in order to induce movement of the diaphragm; and
electronics carried in the housing for driving the one or more transducers.

* * * * *